(12) United States Patent
Maye

(10) Patent No.: US 8,197,863 B2
(45) Date of Patent: Jun. 12, 2012

(54) HOP ACIDS AS A REPLACEMENT FOR ANTIBIOTICS IN ANIMAL FEED

(75) Inventor: John Paul Maye, Washington, DC (US)

(73) Assignee: John I. Haas, Inc., Washington, DC (US)

( * ) Notice: Subject to any disclaimer, the term of this patent is extended or adjusted under 35 U.S.C. 154(b) by 0 days.

(21) Appl. No.: 12/789,120

(22) Filed: May 27, 2010

(65) Prior Publication Data

US 2010/0247708 A1 Sep. 30, 2010

Related U.S. Application Data

(60) Continuation of application No. 12/011,477, filed on Jan. 25, 2008, now abandoned, which is a division of application No. 11/499,502, filed on Aug. 4, 2006, now abandoned, which is a division of application No. 10/668,883, filed on Sep. 23, 2003, now Pat. No. 7,090,873.

(60) Provisional application No. 60/413,246, filed on Sep. 23, 2002.

(51) Int. Cl.
  *A23K 1/17* (2006.01)
  *A23K 1/18* (2006.01)
  *A01N 65/00* (2009.01)

(52) U.S. Cl. ............................ 424/725; 424/442; 426/2

(58) Field of Classification Search .................... None
See application file for complete search history.

(56) References Cited

U.S. PATENT DOCUMENTS

| | | | |
|---|---|---|---|
| 1,400,161 A | | 12/1921 | Heinemann |
| 2,898,209 A | | 8/1959 | Murtaugh et al. |
| 3,821,416 A | | 6/1974 | Thompson et al. |
| 4,148,873 A | | 4/1979 | Owades |
| 5,114,708 A | * | 5/1992 | Hunter et al. |
| 5,286,506 A | | 2/1994 | Millis et al. |
| 5,455,038 A | | 10/1995 | Barney et al. |
| 5,827,895 A | | 10/1998 | Nutter et al. |
| 6,313,178 B1 | | 11/2001 | Nutter et al. |
| 6,391,346 B1 | * | 5/2002 | Newmark et al. |
| 6,423,317 B1 | * | 7/2002 | Haas et al. |
| 7,090,873 B2 | | 8/2006 | Maye |
| 2001/0014365 A1 | | 8/2001 | Johnson et al. |
| 2002/0086062 A1 | | 7/2002 | Kuhrts |

FOREIGN PATENT DOCUMENTS

| | | |
|---|---|---|
| DE | 20022307 U1 | 8/2001 |
| EP | 1277473 A1 | 1/2003 |
| GB | 120166 A | 10/1918 |
| GB | 132597 A | 9/1919 |
| GB | 2072657 A * | 10/1981 |
| GB | 2330076 A * | 4/1999 |
| JP | 01172340 A | 7/1989 |
| JP | 01172341 A | 7/1989 |
| RU | 2075298 C1 | 3/1997 |
| WO | 01/76614 A1 | 10/2001 |

OTHER PUBLICATIONS

Krishna, G et al. Agricultural Wastes (1986); 17(2): 99-117. Fermentation of various preparations of spent hops (*Humulus lupulus* L.) using the rumen simulation technique (Rusitec).*

Beuchat et al., "Antimicrobials Occurring Naturally in foods", Food Technology, Institute of Food Technologists, 43(1), pp. 134-142 (1989).

C. Krishna et al., "Fermentation of various preparations of spent hops (*Humulus lupulus* L.) using the rumen simulation technique (Rusitec)," Agricultural Waters, 17(2): 99-117 (1986).

W. Windisch et al., "antiseptic action of a-hop-bitter acid and its decomposition products on microorganisms", Wochenschrift fuer Brauerei, vol. 41, pp. 175-220 (1924).

T.K. Walker et al., "Report on the preservative principles of hops. 18. the therretical basis of the log phase method for the evaluation of the bacteriostatic power and the procedure in using phenol as a standard of value", Journ. Inst. Brewing, 34(1), pp. 17-30 (1937).

A. Papadopoulou et al., "The control of selected micro-organisms during the malting process", Journal of the Institute of Brewing, 106(3), pp. 179-188 (2000).

G.J. Mannering et al., "Effects of the hop component, coupulone, on the induction of cytochrome P4503A and the replication of human tumour cells", Food Nutrition and Chemical Toxicity, pp. 311-323 (1993).

A.F. Schmalreck et al., "Structural features determining the antibiotic potencies of natural and synthetic hop bitter resins, their precursors and derivatives", Can. J. Microbiol., vol. 21, pp. 205-212 (1975).

J.C. Lewis et al., "Lupulon and humulon—Antibiotic constituents of hops", J. Clin. Invest., 28(5 Pt. 1), pp. 916-919 (1949).

Y.C. Chin et al., "Antituberculous activity and toxicity of lupulon for the mouse", Proceedings of the Society for Experimental Biology and Medicine, vol. 70, pp. 158-162 (1949).

R.J. Arnould et al., "L'utillisation de dreches de brasserie (malt et houblon) dans l'alimentation des vaches laitieres", Revue de l'Agric, vol. 36, pp. 93-105 (1983).

PTO 07-5751—Translation of L'utilisation de dreches de brasserie (malt et houblon) dans l'alimentation des vaches laiteres: The use brewery dregs (malt and hops) in the feeding of dairy cows by R. Arnould—Translation by: FLS, Inc.

* cited by examiner

*Primary Examiner* — Michele C. Flood
(74) *Attorney, Agent, or Firm* — Jeffrey D. Hsi; Dwight D. Kim; Edwards Wildman Palmer LLP

(57) ABSTRACT

A method of using hop acids for increasing food and energy uptake from feed by livestock is described which includes delivering the hop acids for oral ingestion to the animals by mixing the acids with livestock feed. The acids are mixed with the feed in an amount to inhibit certain types of undesirable bacteria in the livestock's digestive system, thereby increasing the production of propionate and lactate and decreasing the production of methane gas.

8 Claims, No Drawings

HOP ACIDS AS A REPLACEMENT FOR ANTIBIOTICS IN ANIMAL FEED

CROSS-REFERENCE TO RELATED APPLICATIONS

This application is a continuation of U.S. patent application Ser. No. 12/011,477, filed Jan. 25, 2008, which is a divisional of U.S. patent application Ser. No. 11/499,502, filed Aug. 4, 2006, which is a divisional of U.S. patent application Ser. No. 10/668,883, filed Sep. 23, 2003, which claims benefit of U.S. provisional application 60/413,246, filed Sep. 23, 2002, the contents of each is incorporated by reference herein.

BACKGROUND OF THE INVENTION

The present invention is directed to an organic food supplement and an animal feed. In particular, the invention is directed at replacing antibiotics in animal feed with hop acids.

Livestock, such as cattle, chickens, and pigs, are fed some of the cheapest foodstuffs that farmers can purchase. Animals that graze and eat low quality feed are subject to a diet contaminated with bacteria and protozoa. The rumen of farm animals is a complex system composed of a variety of bacteria and protozoa. Most of the gram-negative bacteria are beneficial to food and energy uptake, commonly referred to as "good" bacteria and protozoa, while gram-positive bacteria and protozoa reduce food and energy uptake, commonly referred to as "bad" bacteria and protozoa. Antibiotics in animal feed can kill bacteria and protozoa which negatively impact animal growth. However, high levels of antibiotics can sterilize the rumen causing the animal to become sick, and in some cases, die. Therefore, very low levels of antibiotics are used to control harmful bacteria in the rumen.

High levels of microorganisms within the animal's digestive track can reduce food intake efficiency and cause the animal to become sick and even die. Inefficient utilization of feed also adversely effects the environment by increasing production of animal waste products containing high nitrate levels and increasing animal methane emission. Horses and zoological animals also experience digestive disorders due to bacteria and protozoa infection.

Ionophores are a class of antibiotics commonly used in animal feed. Ionophores are polyether antibiotics that transport ions across biological membranes. Ionophores are molecules which have several oxygen atoms spaced throughout the molecule. The positions of the oxygen atoms create a cavity that can entrap cations. Ionophores have polar and non-polar regions that enhance cation entrapment and interaction with bacteria cell membranes. Ionophores are effective against gram-positive bacteria and protozoa but not gram-negative bacteria. By killing or controlling the growth of these microorganisms, animal feed efficiency and the health and well being of the animals can be improved.

Many people desire the ability to purchase and consume organic meat and poultry products. For example, Europe heavily regulates the sale, use and importation of non-organic meat and poultry products. Meat and poultry products containing antibiotics are not considered organic products. The use of ionophores in animal feed causes the meat from those animals to be considered non-organic. There is a strong desire to discover alternatives to antibiotics which can be used in animal feed. These and other limitations and problems of the past are solved by the present invention.

BRIEF SUMMARY OF THE INVENTION

A composition and a method of using hop acids as an organic food supplement is shown and described.

A method of using hop acids as an organic food supplement for livestock is described including delivering the hop acids for oral ingestion by mixing the acids with livestock feed. The acids are mixed with the feed in an amount to inhibit certain types of undesirable bacteria in the livestock's digestive system. In one aspect, the amount of hop acid to inhibit certain types of undesirable bacteria in the animal's digestive system is from about 1 ppm to about 30 ppm. The composition and method described allows for the production of antibiotic free livestock.

The invention will best be understood by reference to the following detailed description of the preferred embodiment. The discussion below is descriptive, illustrative and exemplary and is not to be taken as limiting the scope defined by any appended claims.

DETAILED DESCRIPTION OF THE BEST MODE

The hop plant, *Humulus lupulus*, produces organic acids known as alpha acids (humulone) and beta acids (lupulone). These hop acids include but are not limited to alpha acids and beta acids but also their isomerized forms, reduced forms and salts. Beta acids include lupulone, colupulone, adlupulone as well as other analogs. Alpha acids include humulone, cohumulone, adhumulone, posthumulone, and prehumulone, as well as other analogs. They consist of a complex hexagonal molecule with several side chains, with ketone and alcohol groups. Each different humulone differs in the make-up of the side chain. Alpha acids are known to isomerize when exposed to heat to fowl isoalpha acids. Isoalpha acids and its reduced forms, namely rho-isoalpha acids, tetrahydroisoalpha acids and hexahydroisoalpha acids are hop acids commonly used to flavor beer.

Ionophore antibiotics are effective at killing and inhibiting the growth of many gram-positive bacteria and protozoa but not gram-negative bacteria. Like ionophore antibiotics, hop acids are also known to be effective at killing and inhibiting the growth of gram-positive bacteria and protozoa but not gram-negative bacteria. U.S. Pat. No. 6,379,720 discloses that beta acids are known to kill and inhibit the growth of algae. U.S. Pat. No. 6,352,756 and U.S. Pat. No. 6,423,317 disclose that some hop acids such as alpha acids, beta acids, isoalpha acids and tetrahydroisoalpha acids are known to kill protozoa commonly found in rivers and lakes. Algae and protozoa are in the same kingdom, Protoctista, and both are unicellular organisms. Both ionophores and hop acids work by disrupting the pH levels within a bacteria cell eventually causing it to stop growing or die. Hop acids are also known to have a polar and a non-polar region and are very good at trapping cations.

The major gas excreted by farm animals is carbon dioxide ($CO_2$), which is a fully oxidized carbon source. Methane ($CH_4$) an unoxidized carbon source is considered lost energy to the farm animal and is an environmental pollutant. It is estimated that about 2-12% of farm animal energy is lost due to methane gas excretion. As a result of this lost energy, the cost for feeding animals is increased. It is believed that farm animals are responsible for about 15-20% of the methane found in the atmosphere. This increase in methane is responsible in part for global warming which negatively impacts the environment.

The introduction of low levels of beta acid, alpha acids, isomerized and reduced alpha acids into an artificial rumen shows positive effects in barley and corn (starch) fermentation and alfalfa (fiber) fermentation. Beta acids as low as 2 ppm increased propionate levels in barley fermentation by 97% and 56% in alfalfa fermentation. An increase in propionate concentration is significant since propionate makes-up about 50% of the carbon source used by animals for growth.

Also, a beta acid concentration of 2 ppm in the artificial rumen caused a reduction in butyrate levels by 84% in barley and 35% in alfalfa. Butyrate is an intermediate toward the production of methane. Reduction of butyrate means a reduction in methane. The reduction in methane provides the added benefit of helping the environment by reducing greenhouse gas emissions. Bacterial purine assay shows a 60% reduction in bacteria content in barley fermentation. Overall, beta acids significantly enhanced the carbon source build-up via propionate and increased energy uptake by the animal by reducing butyrate production.

In another embodiment, hop acids may be added to nutritional supplements for livestock animals. The following test procedures were utilized in each of the in vitro examples set forth herein. Barley and alfalfa feeds were fermented in an artificial gut using rumenal fluid containing a bacterial mixture commonly found in cattle. The rumen is made-up of a complex mixture of bacteria and protozoa. Gram negative bacteria are generally considered beneficial since they contribute to the break-down of cellulose into compounds beneficial for animal growth and energy. Gram positive bacteria and protozoa are generally not beneficial since their digestive byproducts are not beneficial to the animal. The gram positive organisms that need to be controlled include *Ruminococcus albus*, *R. flavefaciens* and *Butyrivibrio fibrisolvens*. Controlling these micro-organisms has the beneficial effect of decreasing fermentation thus allowing more energy nutrients to go to the animal. Controlling the bacterium *Methanobacterium ruminatium* reduces the conversion of $H_2$ to methane gas. Controlling the various species of *Streptococci* and *Lactobacilli* also reduce the undesirable use of $H_2$ and allows more to be used in the desirable formation of propionate. Proprionate is largely responsible for animal growth. Isotricha and Entodini are two protozoa which commonly infect the rumin. Again they take away energy and nutrients from the farm animal. During the fermentation, "good" and "bad" bacteria were allowed to compete for starch and fiber within these two feeds. Fermentations with low levels of alpha acids, beta acid, isoalpha acids, rho-isoalpha acids, tetrahydro-isoalpha acids and hexahydro-isoalpha acids were tested as well as a control that contained no hop acids. After rumenal fermentation was completed, end products were assayed to determine the effects of these hop acids.

Example 1

Table 1 shows that as little as 1.25 ppm of beta acid reduces gas production by about 40% in Barley and 30% in Alfalfa. Slow gas production rates generally mean the rumen is converting more of the valuable foodstuffs into energy and carbon for animal growth. High gas production rates usually means higher levels of methane in the gas, thus low food and low energy uptake. In Table 1 below, SE means standard error.

TABLE 1

In Vitro Gas Production

| Item | Level of Beta Acids, ppm | | | | SE |
|---|---|---|---|---|---|
| | 0 | 1.25 | 2.5 | 3.75 | |
| Barley Rate of Production | | | | | |
| %/hr | 9.1 | 9.1 | 8.9 | 8.6 | 0.1 |
| Total Gas, mL/72 h | 404.3 | 242.3 | 273.0 | 265.2 | 8.0 |
| Alfalfa Rate of Production | | | | | |
| %/hr | 9.1 | 8.9 | 8.8 | 8.8 | 0.0 |
| Total Gas, mL/72 h | 431.3 | 312.7 | 303.0 | 308.3 | 5.2 |

Example 2

Table 2 shows the amount of fiber in barley and alfalfa feed. This test method is used to measure fiber in feed. The fiber is generally cellulose, hemicellulose and ligan.

TABLE 2

In Vitro Substrate Disappearance

| Item | Level of Beta Acids, ppm | | | | SE |
|---|---|---|---|---|---|
| | 0 | 1.25 | 2.5 | 3.75 | |
| Barley Disappearance, % | | | | | |
| Dry Matter | 68.2 | 60.3 | 64.8 | 59.8 | 0.9 |
| Starch | 87.8 | 75.0 | 82.4 | 77.6 | 0.7 |
| Alfalfa | | | | | |
| Dry Matter | 51.9 | 47.2 | 44.6 | 42.8 | 0.6 |
| NDF | 32.0 | 28.4 | 40.0 | 25.6 | 0.9 |

NDF = Neutral Detergent Fiber.

Example 3

In example 3, lactate was shown to be an end product of in vitro fermentation of barley and alfalfa with beta acids. Table 3 shows an increase in lactate in the artificial rumen. Lactate is an intermediate in the formation of propionate. One concern with increasing lactate levels is a drop in pH. Lactate is a fairly strong acid and low pH's in the rumen reduces food and energy uptake. In this example, the fact that the pH did not drop was an unexpected benefit. The beta acids are able to control harmful bacteria, thus allowing the formation of more lactate, an intermediate for the production of propionate.

TABLE 3

End Products of In Vitro Fermentation

| Item | Level of Beta Acids, ppm | | | | SE |
|---|---|---|---|---|---|
| | 0 | 1.25 | 2.5 | 3.75 | |
| Barley | | | | | |
| pH | 5.1 | 4.9 | 4.9 | 4.9 | 0.0 |
| Lactate μg/mL | 82.9 | 317 | 319 | 257 | 19.1 |
| Alfalfa | | | | | |
| pH | 5.6 | 6.0 | 5.9 | 5.8 | 0.0 |
| Lactate μg/mL | 22.8 | 26.1 | 27.7 | 30.6 | 3.2 |

Example 4

In Example 4, barley was allowed to ferment in an artificial gut to which 1.25 ppm, 2.5 ppm or 3.75 ppm of beta acids were added and the volatile fatty acid end products of the in vitro fermentation of barley were measured. Beta acids are effective at killing and inhibiting the growth of gram-positive bacteria and protozoa but not gram-negative bacteria. Since acetate is formed by the gram-negative bacteria, *B. rumini-cola*, it is not expected that beta acids would control the formation of acetate. However, a slight reduction in acetate levels is expected if propionate levels increase. Table 4 clearly shows that beta acids aid in the formation of propionate. As the amount of beta acid increases in the synthetic gut, the amount of proprionate increases. A 97% increased in propionate concentration is a very significant and positive increase since propionate leads to animal growth. An 84% reduction in butyrate is also very good since butyrate is eventually broken down by the gram-positive bacteria, *Methanobacterium ruminantim*, into methane, which is lost energy. Thus it appears beta acids are controlling the gram-positive bacteria *Ruminococcus albus, R. Flavefaciens, Butyrivirio fibrisolvens*, which are responsible for butyrate production. The results in table 4 show an increase in propionate (carbon source) and a decrease in butyrate, which results in lost energy to the farm animal.

TABLE 4

End Products of In Vitro Fermentation-Barley

| | Level of Beta Acids, ppm | | | | |
|---|---|---|---|---|---|
| Item | 0 | 1.25 | 2.5 | 3.75 | SE |
| Total VFA μmol/mL | 213.8 | 146.0 | 195.5 | 188.8 | 3.8 |
| Acetate | 36.3 | 53.4 | 44.3 | 40.2 | 0.7 |
| Propionate | 25.9 | 36.3 | 50.7 | 51.2 | 0.5 |
| Butyrate moles/100 moles | 35.0 | 8.3 | 5.6 | 5.7 | 0.6 |

Example 5

In Example 5, alfalfa was allowed to ferment in an artificial gut to which 1.25 ppm, 2.5 ppm or 3.75 ppm of beta acids were added and the volatile fatty acid end products of the in vitro fermentation of alfalfa were measured. As in Example 4, it is not expected that beta acids would control the formation of acetate, which is formed by gram-negative bacteria. Yet, as the acetate levels decrease, table 5 shows that 1.25-2.5 ppm of beta acids is responsible for a 56% increase in propionate production. Butyrate levels are also reduced by 35%. Consequently, methane emission is reduced, energy efficiency is enhanced, and animal growth is increased. In Table 1 below, SE means standard error.

TABLE 5

End Products of In Vitro Fermentation-Alfalfa

| | Level of Beta Acids, ppm | | | | |
|---|---|---|---|---|---|
| Item | 0 | 1.25 | 2.5 | 3.75 | SE |
| Total VFA μmol/mL | 232.5 | 206.9 | 198.2 | 204.7 | 6.7 |
| Acetate | 61.4 | 52.7 | 52.4 | 51.4 | 0.3 |
| Propionate | 24.3 | 36.7 | 38.6 | 38.8 | 0.4 |
| Butyrate moles/100 moles | 10.1 | 7.9 | 6.5 | 6.4 | 0.2 |

Example 6

As shown in Table 6, beta acids significantly decrease protozoa such as isotrichia by 86% and entodiniomorph by about 25% in barley fermentation. Bacterial purine, which is a measurement of total bacteria, shows a significant decrease in barley fermentation by 60%. There appears to be no effect on alfalfa protozoa and alfalfa bacterial purine by the beta acids. Again, reduction in protozoa and bacteria levels means more food and energy for animal growth.

TABLE 6

In Vitro Microbe Measurements

| | Level of Beta Acids, ppm | | | | |
|---|---|---|---|---|---|
| Item | 0 | 1.25 | 2.5 | 3.75 | SE |
| Barley Protozoa × 10³ | | | | | |
| Isotrichia, no./mL | 14.0 | 9.7 | 2.0 | 1.7 | 3.4 |
| Entodiniomorph spp no./mL | 10.0 | 11.7 | 7.7 | 4.7 | 2.7 |
| Bacterial purine, mg/tube | 63.3 | 28.5 | 25.9 | 23.7 | 5.7 |
| Alfalfa Protozoa × 10³ | | | | | |
| Isotrichia, no./mL | 1.0 | 1.0 | 4.0 | 2.7 | 0.7 |
| Entodiniomorph spp no./mL | 1.7 | 1.7 | 3.3 | 1.7 | 0.9 |
| Bacterial purine, mg/tube | 49.8 | 44.1 | 33.1 | 38.1 | 5.7 |

Example 7

As shown in Table 7, the effect of hop acids on gas production, end product production, and microbial growth in in vitro fermentation was shown in alfalfa. The tests included a control group C treated with no alpha acids or beta acids, group A given 2 ppm of alpha acids, group B given 2 ppm of beta acids, group H given 2 pm hexahydroisoalpha acids, group I given 2 ppm isoalpha acids, group R given 2 ppm rho-isoalpha acids, group T given 2 ppm tetrahydroisoalpha acids, and group M given 6 ppm of the antibiotic monensin available from Eli Lilly of Indianapolis, Ind. The rumen is the primary site for the action of monensin in the cow. Monensin is available in various forms for use in cattle and has been available for use in beef cattle and heifers for about 20 years. It can be incorporated into feed as a powder or given as a rumenal bolus by the use of a variable geometry device, also called a controlled-release capsule. The capsule consists of a plastic cylinder with folding wings at one end, which allow the capsule to be retained in the rumen. These capsules, which contain 32 gm of monensin released over 100 days, have proved to be a useful means of conducting large randomized controlled trials. A typical inclusion rate for monensin in feed is 10 to 30 mg per kg of finished feed.

Monensin acts to selectively decrease populations of certain rumen bacteria. It does this by modifying the movement of ions across cell membranes. Gram positive bacteria from the rumen produce hydrogen, ammonia, lactate, acetate, and methane and are more sensitive to monensin, while the gram negative bacteria which produce propionate and succinate are less susceptible. Differences in cellular membrane structure between gram-positive and gram-negative bacteria are chiefly responsible for the different sensitivities of bacteria to monensin. Some species of gram-positive bacteria, however, adapt over time to the presence of monensin and some gram-negative species are sensitive to high concentrations of monensin. Gram positive bacteria produce less methane when monensin is added to the diet.

As shown in Table 7, nearly all six of the hop acids tested showed positive effects on rumen fermentation. Although alpha acids and rho-isoalpha acids did not reduce the rate of total gas production, beta acids (group B), hexahydroisoalpha acids (group H), isoalpha acids (group I) and tetrahydroisoalpha acids (group T) experienced a reduction in rate of gas production, total gas production, and fermentation. Monensin did not reduce gas production, total gas production, and fermentation.

With regards to end products produced, pH was most basic with the introduction of isoalpha acids in group I and remained constant with the introduction of mixed alpha acids. No drop in pH was shown in any of the groups.

Lactate, an intermediate for propionate, production increased when the alfalfa fermentation was treated with beta acids (group B), hexahydroisoalpha acids (group H), isoalpha acids (group I) and tetrahydroisoalpha acids (group T). Volatile fatty acid (VFA) production decreased across all groups and most markedly in group I. Yet, specific fatty acid production for acetate increased for alpha acids and rho-isoalpha acids, propionate increased in all groups except for alpha acids. Butyrate increased only with rho-isoalpha acid, and valerate production increased in none of the groups. Proprionate levels were increased significantly with beta acids, isoalpha acids, tetrahydroisolalpha acids and monensin. This may be a function of the increase in lactate, an intermediate in propionate production. With regards to microbial measurements, monensin was found to most effectively eliminate protozoa and bacterial purines from the artificial rumen. With the exclusion of monensin, only group A exhibited any reduction in bacterial purines.

Example 8

As shown in Table 8, the effect of hop acids on gas production, end product production, and microbial growth in in vitro fermentation was shown in barley. The tests included a control group C treated with no alpha acids or beta acids, group A given 2 ppm of alpha acids, group B given 2 ppm of beta acids, group H given 2 pm hexahydroisoalpha acids, group I given 2 ppm isoalpha acids, group R given 2 ppm rho-isoalpha acids, group T given 2 ppm tetrahydroisoalpha acids, and group M given 6 ppm of the antibiotic monensin.

Table 8 shows the effects of hop bitter acids on gas production, end product production, and microbial growth in in vitro fermentation of barley. As shown in Table 8, the introduction of alpha acids did not reduce the rate of total gas production. Isoalpha acids and tetrahydroisoalpha acids experienced a reduction in rate of gas production and all groups experienced a reduction in the total amount of gas produced in a 72 hour period.

With regards to end products produced, as with alfalfa, pH was most basic with the introduction of isoalpha acids. The pH remained constant with the introduction of tetrahydroisoalpha acids. All other groups became more acidic.

Lactate production increased in all groups except monensin. The most marked increase was in I, which was also the most basic group. Volatile fatty acid (VFA) production decreased in groups B and T and, as in alfalfa, most markedly in group I. Propionate increased only in groups B, I and T. Butyrate decreased across all groups relative to the control. It appears that the particular acid which is most effected by the introduction of alpha acids and beta acids into the artificial rumen containing barley is butyrate.

With regards to microbial measurements, no effect was seen on the decrease of bacterial purines with the introduction of any of the alpha acids or beta acids.

TABLE 7

Effects of Hop Acids on In vitro Fermentation - Alfalfa

| Group | C | A | B | H | I | R | T | M | SE |
|---|---|---|---|---|---|---|---|---|---|
| Disappearance | | | | | | | | | |
| DM, % | $63^a$ | $62^{ab}$ | $53^c$ | $46^d$ | $36^f$ | $53^c$ | $41^e$ | $60^b$ | 1.0 |
| NDF, % | $59^a$ | $40^b$ | $27^{bc}$ | $17^{cd}$ | $2^d$ | $31^{bc}$ | $9^d$ | $32^{bc}$ | 5.6 |
| Gas Production | | | | | | | | | |
| Rate, %/hr | $9.2^a$ | $9.2^a$ | $9.0^c$ | $9.0^c$ | $9.1^b$ | $9.0^c$ | $9.1^b$ | $9.2^a$ | 0.0 |
| Total, mL/72 hr | $304^a$ | $328^a$ | $262^b$ | $242^b$ | $150^d$ | $307^a$ | $202^b$ | $320^a$ | 12.6 |
| mL/g fermented | $238^b$ | $265^a$ | $246^b$ | $261^{ab}$ | $207^b$ | $287^a$ | $247^b$ | $263^{ab}$ | 14.6 |
| End Products | | | | | | | | | |
| pH | $5.7^g$ | $5.7^g$ | $6.0^e$ | $6.2^c$ | $6.6^a$ | $6.1^d$ | $6.4^b$ | $5.8^f$ | 0.0 |
| Lactate, g/mL | $52^d$ | $48^d$ | $63^d$ | $83^b$ | $168^a$ | $46^d$ | $68^c$ | $38^d$ | 5.3 |
| VFA, mol/mL | $269^a$ | $257^a$ | $184^c$ | $173^c$ | $132^d$ | $184^c$ | $146^d$ | $215^b$ | 4.9 |
| Acetate, mole % | $63^b$ | $65^a$ | $54^e$ | $61^c$ | $57^d$ | $64^{ab}$ | $56^d$ | $60^c$ | 0.4 |
| Propionate, mole % | $20^f$ | $20^f$ | $38^a$ | $27^d$ | $37^b$ | $22^e$ | $39^a$ | $31^c$ | 0.2 |
| Butyrate, mole % | $10^b$ | $10^b$ | $6^c$ | $10^b$ | $5^d$ | $13^a$ | $4^e$ | $6^c$ | 0.2 |
| Valerate, mole % | $2^a$ | $2^a$ | $1^b$ | $1^b$ | $0^c$ | $1^b$ | $0^c$ | $2^a$ | 0.1 |
| Microbe Measurements Protozoa × 10³ | | | | | | | | | |
| Isotrichia, no/mL | $2^a$ | $2^a$ | $0.3^b$ | $0.3^b$ | $0^c$ | $0.3^b$ | $0.7^b$ | $0^c$ | 0.5 |
| Entodinia, no/mL | $20^a$ | $22^a$ | $14^{ab}$ | $13^{ab}$ | $22^a$ | $9^b$ | $21^a$ | $6^c$ | 2.7 |
| Bacterial purines, mg/tube | $3.2^{bc}$ | $3.1^{bc}$ | $3.4^{abc}$ | $5.0^a$ | $4.7^{ab}$ | $3.2^{bc}$ | $4.0^{abc}$ | $2.6^c$ | 0.4 |

(C) control, (A) alpha acids (2 ppm), (B) beta acids (2 ppm), (H) hexahydroisoalpha acids (2), (I) isoalpha acids (2 ppm), (R) rho-isoalpha acids (2), (T) tetrahydroisoalpha acids (2 ppm) and (M) the antibiotic monensin (6 ppm)
$^{a,b,c}$Means with different superscripts differ (P < 0.01)

TABLE 8

Effects of Hop Acids on In vitro Fermentation - Barley

| Group | Treatment | | | | | | | | |
|---|---|---|---|---|---|---|---|---|---|
| | C | A | B | H | I | R | T | M | SE |
| Disappearance | | | | | | | | | |
| DM, % | 85$^a$ | 78$^c$ | 74$^d$ | 72$^e$ | 69$^f$ | 70$^{ef}$ | 72$^{de}$ | 83$^b$ | 0.7 |
| Starch, % | 98$^{ab}$ | 100$^a$ | 97$^{bc}$ | 98$^{ab}$ | 89$^b$ | 92$^d$ | 94$^{cd}$ | 99$^a$ | 0.0 |
| Gas Production | | | | | | | | | |
| Rate, %/hr | 9.0$^{bc}$ | 9.1$^a$ | 9.2$^a$ | 9.0$^{bc}$ | 8.9$^d$ | 9.1$^{bc}$ | 8.9$^d$ | 9.1$^b$ | 0.0 |
| Total, mL/72 hr | 345$^a$ | 278$^d$ | 246$^e$ | 295$^{cd}$ | 316$^b$ | 297$^{bcd}$ | 303$^{bc}$ | 336$^a$ | 6.5 |
| mL/g fermented | 208$^c$ | 187$^d$ | 171$^e$ | 213$^{bc}$ | 238$^a$ | 222$^b$ | 218$^{bc}$ | 212$^{bc}$ | 4.0 |
| End Products | | | | | | | | | |
| pH | 5.1$^b$ | 4.8$^e$ | 4.7$^f$ | 4.9$^d$ | 5.2$^a$ | 4.9$^d$ | 5.1$^b$ | 5.0$^c$ | 0.0 |
| Lactate, g/mL | 50$^b$ | 58$^{cd}$ | 78$^{abc}$ | 62$^{cd}$ | 95$^{ab}$ | 106$^a$ | 78$^{abc}$ | 36$^d$ | 9.1 |
| VFA, mol/mL | 257$^b$ | 277$^a$ | 227$^c$ | 261$^b$ | 201$^d$ | 257$^b$ | 211$^d$ | 263$^b$ | 3.8 |
| Acetate, mole % | 32$^d$ | 43$^b$ | 37$^c$ | 39$^c$ | 25$^e$ | 46$^a$ | 24$^e$ | 32$^d$ | 0.9 |
| Propionate, mole % | 24$^c$ | 20$^d$ | 37$^a$ | 20$^d$ | 29$^b$ | 16$^e$ | 30$^b$ | 24$^c$ | 0.9 |
| Butyrate, mole % | 33$^a$ | 24$^c$ | 14$^e$ | 28$^b$ | 23$^d$ | 29$^b$ | 22$^d$ | 28$^b$ | 0.5 |
| Valerate, mole % | 8$^d$ | 12$^c$ | 11$^c$ | 12$^c$ | 23$^a$ | 8$^d$ | 24$^a$ | 14$^b$ | 0.5 |
| Microbe Measurements Protozoa × 10$^3$ | | | | | | | | | |
| Isotricha, no/mL | 0.7 | 0.3 | 0 | 0.3 | 0.3 | 0.3 | 0 | 0 | 0.3 |
| Entodinia, no/mL | 82$^a$ | 41$^b$ | 43$^b$ | 33$^b$ | 50$^b$ | 35$^b$ | 37$^b$ | 38$^b$ | 6.0 |
| Bacterial purines, mg/tube | 1.3$^c$ | 1.8$^b$ | 2.0$^{ab}$ | 2.1$^{ab}$ | 1.7$^b$ | 2.0$^{ab}$ | 1.3$^b$ | 1.5$^b$ | 0.1 |

C) control, (A) alpha acids (2 ppm), (B) beta acids (2 ppm), (H) hexahydroisoalpha acids (2), (I) isoalpha acids (2 ppm), (R) rho-isoalpha acids (2), (T) tetrahydroisoalpha acids (2 ppm) and (M) the antibiotic monensin (6 ppm)
$^{a,b,c}$Means with different superscripts differ (P < 0.01)

Example 9

As shown in Table 9, the effect of hop acids on gas production, end product production, and microbial growth in in vitro fermentation was shown in barley. The tests included a control group C treated with no alpha acids or beta acids, group A given 2 ppm of alpha acids, group B given 2 ppm of beta acids, group H given 2 pm hexahydroisoalpha acids, group I given 2 ppm isoalpha acids, group R given 2 ppm rho-isoalpha acids, group T given 2 ppm tetrahydroisoalpha acids, and group M given 6 ppm of the antibiotic monensin.

As shown in Table 9, the rate and total gas production decreased in all groups except in the control and in monensin.

With regards to end products produced, as with alfalfa and barley, pH was most basic with the introduction of isoalpha acids. All other groups became more acidic.

Lactate production increased in all groups. The most marked increase was in group R. The greatest number of groups, as compared to barley and alfalfa, were seen to exhibit a reduction in volatile fatty acid (VFA) production. VFA production decreased in groups B, H, I, and T. Propionate increased only in groups B, I and T. Only valerate increased in all compounds tested.

With regards to microbial measurements, only in corn compared to barley and alfalfa was any decrease in bacterial purines shown for all groups except monensin. Additionally, entodinia was shown to decrease in all groups except monensin.

TABLE 9

Effects of Hop Acids on In vitro Fermentation - Corn

| Group | Treatment | | | | | | | | |
|---|---|---|---|---|---|---|---|---|---|
| | C | A | B | H | I | R | T | M | SE |
| Disappearance | | | | | | | | | |
| DM, % | 90$^a$ | 85$^b$ | 80$^c$ | 76$^d$ | 62$^f$ | 73$^e$ | 73$^e$ | 91$^a$ | 0.7 |
| Starch, % | 91$^{ab}$ | 89$^{ab}$ | 80$^{bc}$ | 79$^{bc}$ | 54$^e$ | 65$^{de}$ | 68$^{cd}$ | 95$^a$ | 0.4 |
| Gas Production | | | | | | | | | |
| Rate, %/hr | 9.1$^a$ | 9.0$^a$ | 9.0$^a$ | 9.0$^a$ | 8.9$^b$ | 9.0$^a$ | 8.9$^b$ | 8.9$^b$ | 0.0 |
| Total, mL/72 hr | 368$^b$ | 309$^c$ | 283$^{de}$ | 288$^d$ | 275$^e$ | 293$^d$ | 313$^c$ | 398$^a$ | 3.8 |
| mL/g fermented | 212$^c$ | 187$^d$ | 187$^d$ | 196$^d$ | 235$^a$ | 210$^c$ | 224$^b$ | 233$^{ab}$ | 3.3 |
| End Products | | | | | | | | | |
| pH | 5.1$^b$ | 4.7$^g$ | 4.8$^f$ | 4.9$^e$ | 5.2$^a$ | 4.9$^d$ | 5.0$^c$ | 5.0$^c$ | 0.0 |
| Lactate, g/mL | 22$^c$ | 87$^b$ | 73$^b$ | 64$^b$ | 86$^b$ | 152$^a$ | 66$^b$ | 58$^{bc}$ | 13.2 |
| VFA, mol/mL | 241$^{bc}$ | 284$^a$ | 231$^{cd}$ | 240$^{bc}$ | 188$^e$ | 245$^{bc}$ | 221$^d$ | 258$^b$ | 6.0 |

TABLE 9-continued

Effects of Hop Acids on In vitro Fermentation - Corn

| Group | Treatment | | | | | | | | SE |
|---|---|---|---|---|---|---|---|---|---|
| | C | A | B | H | I | R | T | M | |
| Acetate, mole % | $35^c$ | $41^a$ | $32^d$ | $35^{cd}$ | $29^e$ | $38^b$ | $25^f$ | $26^f$ | 0.8 |
| Propionate, mole % | $28^c$ | $17^f$ | $39^a$ | $20^{de}$ | $37^b$ | $22^d$ | $36^b$ | $20^e$ | 0.7 |
| Butyrate, mole % | $27^c$ | $30^b$ | $16^e$ | $30^b$ | $18^d$ | $29^b$ | $18^d$ | $35^a$ | 0.5 |
| Valerate, mole % | $6^f$ | $12^d$ | $12^d$ | $15^c$ | $16^{bc}$ | $10^e$ | $20^a$ | $17^b$ | 0.5 |
| Microbe Measurements Protozoa × $10^3$ | | | | | | | | | |
| Isotricha, no/mL | 0.3 | 0 | 0 | 0.7 | 0.7 | 0 | 0 | 0.7 | 0.4 |
| Entodinia, no/mL | $17^d$ | $27^{bcd}$ | $22^{cd}$ | $40^a$ | $37^{ab}$ | $37^{ab}$ | $37^{ab}$ | $28^{bc}$ | 3.5 |
| Bacterial purines, Mg/tube | $1.2^{ab}$ | $1.1^{abc}$ | $0.9^{abc}$ | $0.8^b$ | $1.0^{abc}$ | $0.6^c$ | $0.9^{abc}$ | $1.4^a$ | 0.1 |

C) control, (A) alpha acids (2 ppm), (B) beta acids (2 ppm), (H) hexahydroisoalpha acids (2), (I) isoalpha acids (2 ppm), (R) rho-isoalpha acids (2), (T) tetrahydroisoalpha acids (2 ppm) and (M) the antibiotic monensin (6 ppm)
$a,b,c$Means with different superscripts differ (P < 0.01)

Hop acids can be used for increasing food and energy uptake from feed by poultry, such as chickens and turkeys, by delivering the hop acids for oral ingestion to the animals by mixing the hop acids with feed. The acids are mixed with the feed in an amount to inhibit certain types of undesirable bacteria in the digestive system. Mixing the hop acids with poultry feed may also prevent the poultry from susceptibility to various bacterial and protozoan diseases. An effective amount of hop acids ranges from about 1 ppm to about 30 ppm in poultry feed may increase energy uptake and inhibit certain types of bacteria and protozoa. Further, a range of from about 1 ppm to about 20 ppm, or from about 1 ppm to about 10 ppm, or from about 1 ppm to about 5 ppm, or about 2 ppm of hop acids in poultry feed may increase energy uptake and inhibit certain types of bacteria and protozoa.

As an example of poultry, the chicken has a simple digestive system, with few to no microorganisms living in the digestive system to help digest food like in ruminants such as cattle. Chickens depend on enzymes to aid in breaking down food so it can be absorbed, much like humans.

The crop is a pouch fowled from the esophagus to serve as a storage area for the food until it can be passed along for digestion in the gizzard and intestines. The proventriculus is the true stomach of the bird from which hydrochloric acid and pepsin is secreted to aid in digestion. The muscles of the gizzard are extremely strong and are used to grind or crush the food particles. This process is aided by the presence of grit and gravel picked up by the bird. The digestion and absorption of food takes place primarily in the small intestine. The small intestine is similar to mammals, there are two blind pouches or ceca, about 4-6 inches in length at the junction of the small and large intestine. The large intestine is short, consisting mostly of the rectum about 3-4 inches in length. The rectum empties into the cloaca and feces are excreted through the vent. It usually takes about 2.5 hours for food to pass through the digestive tract from beak to cloaca.

Like cattle, chickens suffer from a diet contaminated with bacteria and protozoa. For example, coccidiosis is a common illness found in chickens. It occurs when a chicken consumes the protozoa coccidia. The coccidia causes lesions in the digestion track of chickens which later become infected by the gram positive bacteria *Clostridium perfringens*. This one-two punch causes many chickens to become very sick and even die. Low levels of antibiotics are used in chicken feed to kill the protozoa cocidia and the gram positive bacteria *clostridium*. Given that hop acids are also effective at controlling the growth of protozoa and gram positive bacteria, it is likely that chickens can benefit from a diet containing hop acids.

Example 10

Seven samples of hop acids were tested for minimum inhibitory concentration (MIC) testing against a strain of *Clostridium perfringens*. The strain of *C. perfringens* (CP-6) was obtained from Colorado Quality Research, Inc.

The bacterial culture and all hop acids were refrigerated until use. The seven hop acids were assayed (identified below by trademark). All were at approximately 1% concentration:

Isohop™; 1.0%

Betastab™ 10A; 0.96%

Alphahop™; 0.93%

Tetrahop™; 1.0%

Hexahop™; 0.97%

HHBA™; 1.0%

Redihop™; 1.0%

*C. perfringens* CP-6 was propagated anaerobically in BHI (pH 7.2). Growth was for 24 h at 35-37° C. After 24 h, the population of the stock culture was approximately $10^8$ cfu/ml.

Hop acids were added to 10 ml tubes of BHI to final concentrations of 80 ug/ml. Chloramphenicol was added to a 10 ml tube to a final concentration of 80 ug/ml as the positive control. Tubes were inoculated with 100 ul of the stock culture and incubated anaerobically at 35-37° C. for 24 h.

For the MIC study, two-fold dilutions of each hop acid were added to 10 ml tubes of BHI, starting at a high concentration of 80 ug/ml and a low concentration of 2.5 ug/ml. Chloramphenicol at 80 ug/ml was used as the positive control. Culture was inoculated to a final concentration of $3.0\times10^6$ cfu/ml and the tubes were incubated as above. At 24 h, optical densities were read at 405 nm, and cell populations were determined.

For hop acids showing complete inhibition at 2.5 ug/ml, dilution schemes were carried out further at 1.25, 0.625, 0.312, and 0.156 ug/ml.

All hop acids showed complete inhibition of *C. perfringens* CP-6 at 80 ug/ml. The following table shows the MIC for all hop acids tested.

| Acid | MIC |
| --- | --- |
| Isohop ™ | 63.0 ug/ml |
| Betastab ™ | 5.7 ug/ml |
| Alphahop ™ | 56.0 ug/ml |
| Tetrahop ™ | 14.0 ug/ml |
| Hexahop ™ | 7.5 ug/ml |
| HHBA ™ | 0.39 ug/ml |
| Redihop ™ | 53.0 ug/ml |

For the propagation of *C. perfringens* CP-6, BHI (pH 7.2) was found to be adequate. Culture population reached $10^8$ cfu/ml in 24 hr when incubated anaerobically at 35-37° C. To ensure that the assay was working properly, the culture was challenged with 80 ug/ml of each hop acid in BHI. At this concentration, all hop acids showed complete inhibition of the culture.

MIC assays showed that HHBA™ (MIC 0.39 ug/ml) was superior to all other hop acids in inhibiting *C. perfringens* CP-6 at pH 7.2. It showed almost a 15-fold greater MIC than the next most effective hop acid, Betastab™. Betastab™ (MIC 5.7 ug/ml) and Hexahop™ (MIC 7.5 ug/ml) were the next two most effective hop acids. Tetrahop™ showed a medium level of inhibition (MIC 14.0 ug/ml), while Isohop™ (MIC 63.0 ug.ml), Alphahop™ (MIC 56.0 ug/ml), and Redihop™ (MIC 53.0 ug/ml) were the least inhibitory.

It is apparent from this particular study that the hop acid most effective in inhibiting *C. perfringens* CP-6 at pH 7.2 is HHBA™. Betastab™ and Hexahop™ were also strongly inhibitory under conditions of the study.

Based on the results of Example 10 above, it is believed that hop acids can be added to poultry feed to protect poultry from a variety of bacterial diseases which can be acquired through infected feed. Chickens, turkey, and other avians are susceptible to the following bacteria diseases:

1. Coliform Infections. Problems attributed to coliform infections are often caused by strains of the *Escherichia coli* organism. The primary routes of invasion by the organism are the respiratory system and the gastrointestinal tract. Problems may result from a coliform infection alone as in primary infection or in combination with other disease agents as a complicating or secondary infection. Secondary infections commonly Occur as a part of the classic air sac disease syndrome as a complication with *Mycoplasma gallisepticum* infections.

There are many different strains or serological types within the group of *E. coli* bacteria. Many are normal inhabitants in intestinal tracts of chickens and turkeys and consequently are common organisms in the birds environment. A marked variation exists between different strains in their ability to cause disease. Some are severe and by themselves can cause disease while others are supposedly harmless. All degrees of pathogenicity exist between the two extremes.

2. Fowl Cholera. The causative organism of fowl cholera is *Pasteurella multocida*. Major sources of infection include contaminate water and feed. In the past, properly administered bacterins are helpful in preventing fowl cholera, particularly in turkeys. Their use must be combined with a rigid program of sanitation. Although drugs usually alter the course of a fowl cholera outbreak, affected birds remain carriers and the disease has a tendency to recur when treatment is discontinued. This may necessitate prolonged treatment with drugs added to the feed and water. Sulfa drugs and broad spectrum antibiotics (Penicillin) usually control losses.

3. Necrotic Enteritis. Necrotic enteritis is an acute disease that produces a marked destruction of the intestinal lining of the digestive tract. Common field names such as rot gut, crud and cauliflower gut accurately describe the condition. The cause of the disease is *Clostridium perfringens*, a spore-forming, rod-shaped bacterium. Bacterial organisms and their toxins are the primary cause but coccidiosis may be a contributing factor. Most of the damage to the intestinal lining apparently is due to toxins produced by the bacterial organisms.

In the past, bacitracin or virginiamycin were effective treatments administered in the feed. Bacitracin can also be given in the drinking water. Supportive vitamin treatment may enhance the effectiveness of the treatments.

4. Ulcerative Enteritis. Ulcerative enteritis is an acute or chronic infection of game birds, chickens, turkeys and other domestic fowl. The cause of the disease is *Clostridium colinum*, a spore forming bacterial rod. The infection spreads by the droppings from sick or carrier birds to healthy birds.

In the past, bacitracin and penicillin are the most effective drugs in the treatment and prevention of this disease. If bacitracin was used, incorporation was recommended in the feed at levels up to 200 grams per ton of feed. Addition of bacitracin to the water at the rate of one teaspoon per gallon was recommended in controlling an outbreak of the disease. Penicillin is also used to treat the disease if bacitracin is not effective.

5. *Pullorum* Disease. *Pullorum* disease is an acute or chronic infectious, bacterial disease affecting primarily chickens and turkeys, but most domestic and wild fowl can be infected. The cause is a bacterium named *Salmonella pullorum*. Disease organisms may enter the bird through the respiratory (as in the incubator) or digestive systems.

6. Fowl Typhoid. Fowl typhoid is an infectious, contagious bacterial disease that is usually acute but sometimes chronic. It affects most domestic and wild fowl including chickens, turkeys, ducks, pigeons, pheasants and other game birds. The cause in the bacterium, *Salmonella gallinarum*. Disease organisms may enter the bird through the respiratory or digestive systems.

Prevention and control depend heavily upon basic disease prevention practices including the hatching chicks from disease-free flocks, practicing strict sanitation on the farm, providing clean feed and water, and proper disposal of all dead birds. The causative organism can live outside the bird body for at least six months, thus requiring extra management precautions to break the disease cycle. Drugs cannot be depended upon as a means of typhoid prevention and are not recommended for that purpose. Infected birds may be salvaged using the same drugs as used to salvage *pullorum* infected birds.

7. Botulism. Botulism is a disease caused by the ingestion of a toxin produced by the *Clostridium botulinum* bacterium. All domestic fowl and most wild birds are susceptible to the toxin's effects. Many human deaths have also been attributed to the consumption of food or water containing the toxin.

Botulism is not a bacterial infection, but a condition produced by a byproduct of the bacteria's growth. The organism is common in nature and is widely dispersed in soils. Ingestion of the organism is not harmful. It becomes dangerous only when conditions are favorable for its growth and subsequent toxin formation. The organism grows best under high humidity and relatively high temperature and in an environment containing decaying organic material (plant or animal). The organism requires an environment in which all atmospheric oxygen is eliminated. The organism cannot multiply in the presence of air. Botulism results after the decaying animal or plant material containing the toxin is consumed.

The toxin is one of the most potent discovered by scientists. The toxin is relatively heat stable but may be destroyed by boiling. There are different types of the toxin; types A and C cause the disease in birds while type B frequently produces the disease in man.

Hop acids can be added to poultry feed to protect poultry from a variety of protozoan diseases which can be acquired through infected feed. Chickens, turkey, and other avians are susceptible to the following protozoan diseases.

1. Coccidiosis. As discussed above, coccidiosis is a disease of fowl caused by a microscopic animal or protozoa caused by microscopic animals called coccidia. There are many species of coccidia that can infect fowl, domestic animals and humans. Each species of coccidia is host specific and does not infect a wide variety of animals. Chickens are susceptible to any of nine coccidia species, turkeys are susceptible to seven species and quail are susceptible to at least four different species of coccidia.

Coccidiosis is transmitted by direct or indirect contact with droppings of infected birds. When a bird ingests coccidia, the organisms invade the lining of the intestine and produce tissue damage as the undergo reproduction. The number of infective coccidia consumed by the host is a primary factor as to the severity of the resulting infection. An infection may be mild enough to go unnoticed while a large infective dose of coccidia may produce severe lesions that can cause death. Coccidia are easily transmitted from one house to another on contaminated boots, clothing, free-flying birds, equipment, feed sacks, insects and rodents.

In the past, it was best prevented by addition of a drug, such as coccidiostat, to the feed that controls the growth of coccidia in the digestive tract But, coccidiostats should not be indiscriminately used and recommendations must be followed precisely.

2. Blackhead (Histomoniasis, Enterohepatitis). Blackhead is an acute or chronic protozoan disease of fowl, primarily affecting the cecae and liver. Blackhead is caused by a protozoan parasite called *Histomonas meleagridis*. The organism in passed in the fecal material of infected birds. Free-living blackhead organisms do not survive long in nature, but those in cecal worm eggs may survive for years. Therefore, most blackhead transmission is considered due to ingesting infected cecal worm eggs. Chickens are frequently infected without showing signs of the disease.

Hop acids can prevent the growth or diminish the growth of the above bacteria and protozoans, thereby assisting in the prevention, preventing, or treating poultry susceptible to the above diseases.

The discussion above is descriptive, illustrative and exemplary and is not to be taken as limiting the scope defined by any appended claims.

I claim:

1. A method for decreasing unoxidized carbon waste by livestock comprising:
    administering to the livestock a feed having an effective amount of hop acid capable of decreasing the production of unoxidized carbon sources in a digestive system fluid of the livestock.

2. A method for increasing propionate concentration in a digestive tract in livestock comprising:
    administering to the livestock a feed having an effective amount of hop acid capable of increasing propionate concentration in a digestive system fluid of the livestock.

3. A method for decreasing butyrate concentration in a digestive tract in livestock comprising:
    administering to the livestock a feed having an effective amount of hop acid capable of decreasing the butyrate concentration in a digestive system fluid of the livestock.

4. The method of any one of claims 1-3 wherein the hop acid is selected from at least one of the group consisting of alpha acids, beta acids, isoalpha acids, rho-isoalpha acids, tetrahydroisoalpha acids and hexahydroisoalpha acids.

5. The method of claim 4 wherein the alpha acids are selected from at least one of the group consisting of humulone, cohumulone, and adhumulone.

6. The method of claim 4 wherein the beta acids are selected from at least one of the group consisting of lupulone, colupulone, and adlupulone.

7. The method of any one of claims 1-3 wherein the amount of hop acid is 2 ppm of digestive system fluid.

8. The method of any one of claims 1-3 wherein the livestock is selected from the group consisting of cattle, poultry, horses, pigs, and zoo animals.

* * * * *